United States Patent [19]
Hoffman et al.

[11] Patent Number: 6,165,509
[45] Date of Patent: Dec. 26, 2000

[54] PEGYLATED DRUG COMPLEXED WITH BIOADHESIVE POLYMER SUITABLE FOR DRUG DELIVERY AND METHODS RELATING THERETO

[75] Inventors: Allan S. Hoffman, Seattle, Wash.; Yoshiki Hayashi, Mishima, Japan

[73] Assignee: University of Washington, Seattle, Wash.

[21] Appl. No.: 09/145,062

[22] Filed: Sep. 1, 1998

[51] Int. Cl.[7] ............................. A61K 47/34; A61K 47/32
[52] U.S. Cl. ............................. 424/487; 424/488
[58] Field of Search ...................... 424/487, 488

[56] References Cited

U.S. PATENT DOCUMENTS

| | | | |
|---|---|---|---|
| 4,795,436 | 1/1989 | Robinson | 424/443 |
| 5,077,051 | 12/1991 | Gallopo et al. | 424/485 |
| 5,455,027 | 10/1995 | Zalipsky et al. | 424/78.08 |
| 5,534,269 | 7/1996 | Igari et al. | 424/484 |
| 5,877,224 | 2/1999 | Brocchini et al. | 514/772.3 |

OTHER PUBLICATIONS

Krupers et al., "Complexation Of Poly(Etaylene Oxide) With Poly(Acrylic Acid–Co–Eydroxyetayl Metacrylates)S," *Eur. Polym. J.* 32(6):785–793, 1996.

Sawbney et al., "Biocrodible Hydrogeis Based on Photopolymerized Poly(ethylene glycol–on–poly($\alpha$–hydroxy acid) Diacrylate–Macromes," *Macromolecules* 26:581–587, 1993.

Zalipsky, "Chemistry of polyethylene glycol conjugates with biologically active molecules," *Advanced Drug Delivery Reviews* 16:157–182 (1995).

Zhao and Harris, "Novel Degradable Poly(ethylene glycol) Esters for Drug Delivery," *ACS Symposium Series* 630:458–472, 1997.

*Primary Examiner*—Peter F. Kulkosky
*Attorney, Agent, or Firm*—Seed Intellectual Property Law Group PLLC

[57] ABSTRACT

PEGylated drugs complexed with bioadhesive polymers, wherein the PEGylated drugs comprise a polyethylene glycol covalently bonded to the drugs are disclosed. The PEGylated drug/bioadhesive polymer complex and compositions thereof may be topically administered to body fluids or mucosal tissues. Methods of administering the PEGylated drug/bioadhesive polymer complex and compositions thereof to an animal are also disclosed.

36 Claims, 12 Drawing Sheets

PEGYLATED DRUG COMPLEXED WITH BIOADHESIVE POLYMER SUITABLE FOR DRUG DELIVERY AND METHODS RELATING THERETO

TECHNICAL FIELD

This invention relates generally to a PEGylated drug complexed with bioadhesive polymer and, more specifically, to a PEGylated drug complexed with a bioadhesive polymer wherein the complex is suitable for drug delivery to a mucosal tissue.

BACKGROUND OF THE INVENTION

Polyethylene glycol (PEG) has been widely used in biomaterials, biotechnology and medicine primarily because PEG is a biocompatible, nontoxic, nonimmunogenic and water-soluble polymer (Zhao and Harris, ACS *Symposium Series* 680: 458–72, 1997). In the area of drug delivery, PEG derivatives have been widely used in covalent attachment (i.e., "PEGylation") to proteins to reduce immunogenicity, proteolysis and kidney clearance and to enhance solubility (Zalipsky, *Adv. Drug Del. Rev.* 16:157–82, 1995). Similarly, PEG has been attached to low molecular weight, relatively hydrophobic drugs to enhance solubility, reduce toxicity and alter biodistribution. Typically, PEGylated drugs are injected as solutions.

A closely related application is synthesis of crosslinked degradable PEG networks or formulations for use in drug delivery since much of the same chemistry used in design of degradable, soluble drug carriers can also be used in design of degradable gels (Sawhney et al., *Macromolecules* 26: 581–87, 1993). It is also known that intermacromolecular complexes can be formed by mixing solutions of two complementary polymers. Such complexes are generally stabilized by electrostatic interactions (polyanion-polycation) and/or hydrogen bonds (polyacid-polybase) between the polymers involved, and/or by hydrophobic interactions between the polymers in an aqueous surrounding (Krupers et al., *Eur. Polym J.* 32:785–790, 1996). For example, mixing solutions of polyacrylic acid (PAAc) and polyethylene oxide (PEO) under the proper conditions results in the formation of complexes based mostly on hydrogen bonding. Dissociation of these complexes at physiologic conditions has been used for delivery of free drugs (i.e., non-PEGylated). In addition, complexes of complementary polymers have been formed from both homopolymers and copolymers.

While significant advances have been made in the field of PEGylated drug delivery, there is still a need in the art for novel and improved PEGylated drug delivery formulations, particularly those that are useful in the area of sustained drug delivery. The present invention fulfills these needs, and provides further related advantages.

SUMMARY OF THE INVENTION

In brief, the present invention is directed to a PEGylated drug complexed with a bioadhesive polymer, wherein the PEGylated drug comprises a polyethylene glycol covalently bonded to the drug. Accordingly, in one aspect of the present invention, a PEGylated drug complexed with a bioadhesive polymer is disclosed wherein the PEGylated drug comprises a polyethylene glycol covalently bonded to the drug and wherein the polyethylene glycol has a molecular weight ranging from about 3 kD to about 50 kD, and preferably from about 5 kD to about 30 kD. The drug of the PEGylated drug complexed with a bioadhesive polymer may be either a protein or a peptide, and preferably is a protein. In an alternative embodiment, the drug of the PEGylated drug complexed with a bioadhesive polymer may be a hydrophobic drug (e.g., taxol or paclitaxel).

In another aspect of the present invention, the bioadhesive polymer of the PEGylated drug complexed with a bioadhesive polymer may be either polyacrylic acid, polymethylacrylic, polyethylacrylic acid or chitosan, and preferably is polyacrylic acid. Alternatively, the bioadhesive polymer of the PEGylated drug complexed with a bioadhesive polymer may be either a random block or graft copolymer of one or more of polyacrylic acid, polymethylacrylic or polyethylacrylic acid. In addition, in one embodiment the PEGylated drug complexed with the bioadhesive polymer is stable at or below pH 4, and in another embodiment the PEGylated drug complexed with the bioadhesive polymer is stable up to about pH 7 and degrades at or above about pH 7.

In yet another aspect of the present invention, the PEGylated drug complexed with a bioadhesive polymer may be in combination with free PEG, polyvinylpyrrolidone, polyacrylamide or N-alkyl derivatives thereof, or polyvinyl alcohol. The free PEG, polyvinylpyrrolidone, polyacrylamide or N-alkyl derivatives thereof, or polyvinyl alcohol have molecular weights ranging from about 10 kD to about 500 kD, preferably from about 10 kD to about 200 kD, and more preferably about 18.5 kD.

Instill another aspect of this invention, a method of delivering a drug to a body fluid or mucosal tissue comprising contacting the body fluid or mucosal tissue with the PEGylated drug complexed with a bioadhesive polymer is disclosed. The body fluid or mucosal tissue may be fluid or tissue of the alimentary tract, respiratory tract, eye, nose, vagina, lung, mouth, or throat. Alternatively, the body fluid or mucosal tissue is fluid or tissue of an open wound.

DETAILED DESCRIPTION OF THE INVENTION

Figure 1:
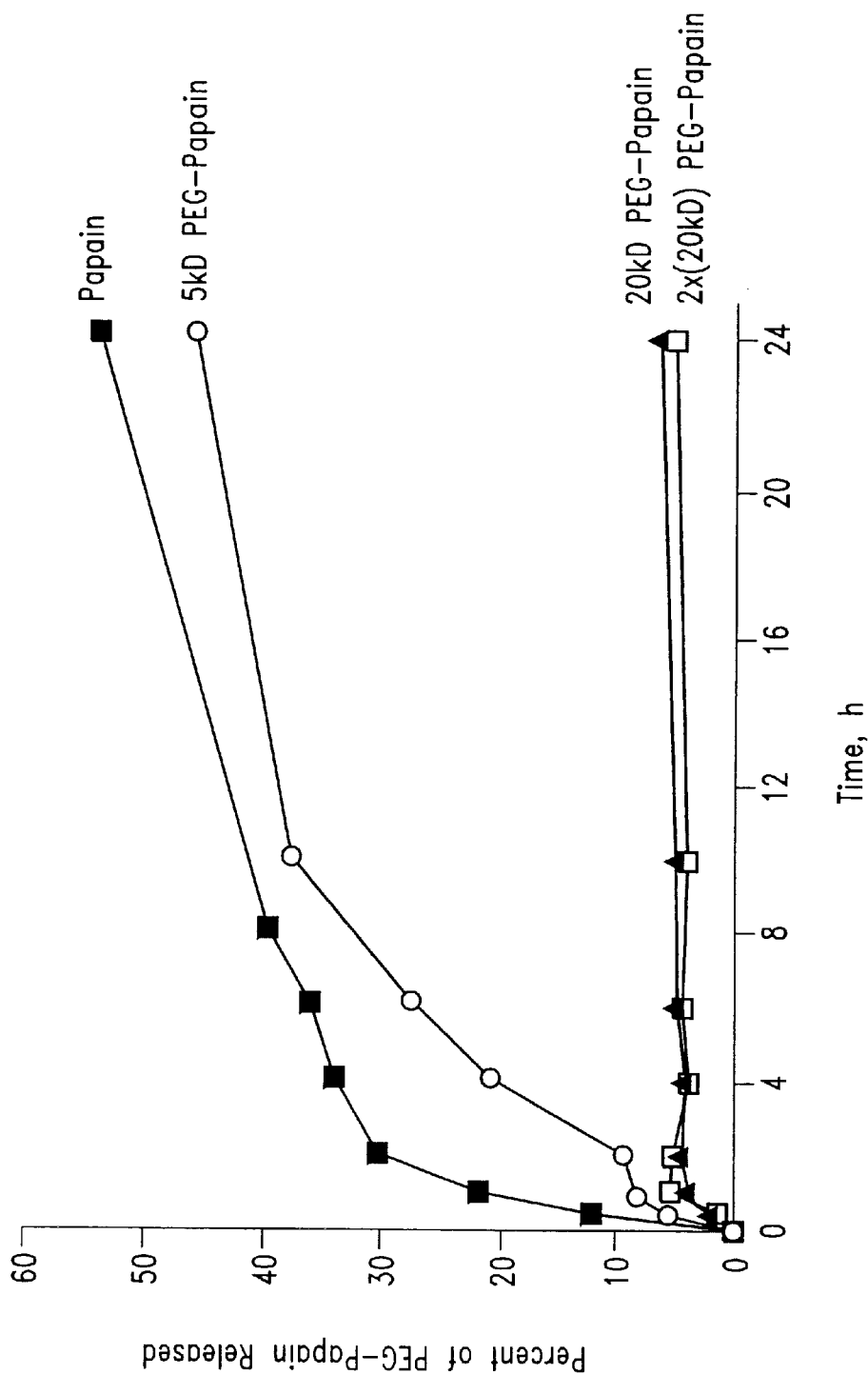
FIG. 1 illustrates the percent release versus time of papain, 5 kD PEG-papain, 20 kD PEG-papain, and 2×20 kDPEG-papain, respectively, from their corresponding formulations (the formulations include polyacrylic acid (PAAc)).

As mentioned above, the present invention is generally directed to a PEGylated drug complexed with a bioadhesive polymer wherein the complex is suitable for sustained drug delivery to a biological fluid or mucosal tissue. More specifically, the PEGylated drug of the present invention comprises a polyethylene glycol (PEG) covalently bonded to a drug.

Covalent attachment of the PEG to the drug (known as "PEGylation") may be accomplished by known chemical synthesis techniques. For example, in one exemplary embodiment of the present invention, the PEGylation of protein may be accomplished by reacting NHS-activated PEG with the protein under suitable reaction conditions as generally depicted by the following reaction scheme:

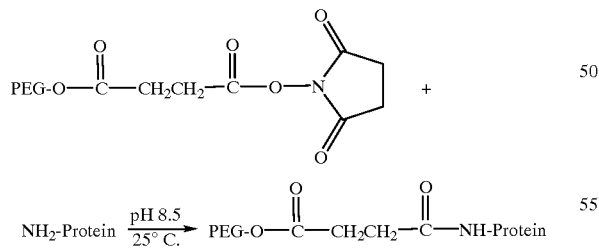

In an alternative embodiment, the PEGylated drug of the present invention comprises a polyethylene glycol (PEG) bonded to a drug via a degradable bond such that after release from the complex with the bioadhesive polymer, the PEGylated drug is subsequently dissociated into drug and PEG. In the context of covalent bonds, the covalent bonds may degrade in aqueous biologic environments by hydrolysis (e.g., an ester —COO—→—COOH+HO—, or an anhydride, —CO—O—CO—→—COOH+HOOC—, or an amide —CONH—→—COOH+$H_2$N—) or by enzymolysis wherein an enzyme may effect similar reactions. Enzymes may also cause oxidation, reduction or other chemical reactions which lead to bond scission.

After PEGylation, the PEGylated drug is complexed with a suitable bioadhesive polymer. As used within the context of the present invention, suitable bioadhesive polymers include (but are not necessarily limited to) polyacrylic acid (PAAc), polymethacrylic acid (PMAAc), polyethylacrylic acid (PEAAc) including lightly cross-linked polymers thereof, and chitosan. More specifically, the first three bioadhesive polymers of the present invention may be generally characterized as carboxylic acid-containing polymers (chitosan, however, contains no carboxyl groups). The carboxylic acid moieties of such polymers are typically nonionized at pHs below 5 and become ionized when contacted with, for example, a biological fluid and/or mucosal tissue at higher pH values. Note the pK of the carboxyl group will generally rise with the hydrophobicity of its microenvironment such that the degree of ionization of the carboxyl group at pH 7.4 will decrease in the order of PAAc, PMAAc, and PEAAc. Thus, the composition of the carboxylic polymer or copolymer will determine the rate and extent of dissociation of its complex with PEG at pH 7.4, since the strength of the complex will depend on the presence of a significant number of repeat units having —COOH groups (as opposed to —COO$^-$ groups).

This feature also influences the bioadhesive properties of the carboxylic polymer via hydration and swelling upon contact with the biological fluid and/or mucosal tissue. For example, the carboxylic acid groups of polymers such as PAAc are ionized upon contact with biological fluids or mucosal tissues, and the uptake of cations (such as $Na^+$ and $K^+$) provides neutralized carboxylic acid moieties (e.g., $COO^-Na^+$). This ionization is accompanied by the uptake of water which, in turn, results in swelling and can cause the polymer to become "sticky" or bioadhesive. For purposes of the present invention, bioadhesive polymers and copolymers may be formed by known chemical synthesis techniques such as by polymerizing suitable monomers to yield the desired polymer or copolymer. Accordingly, a suitable polymer may be derived, for example, from polymerizable carboxylic acids, resulting in the desired synthetic carboxylic acid-containing polymer.

In contrast, the bioadhesivity of chitosan, a poly(D-glucosamide) as generally shown below, is due to its strong acid-base and ionic interactions with the negatively charged mucosal surfaces. Furthermore, chitosan is not polymerized; rather, it is obtained as a polymer of poly(D-glucosamide) from natural sources (e.g., crustaceans).

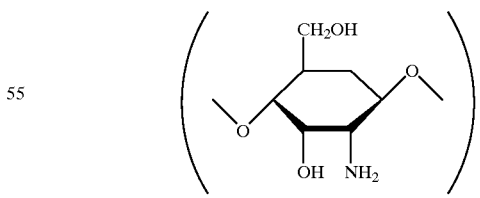

As used in the context of the present invention, the term "drug" includes the definition set forth in 21 C.F.R § 201(g)(1), "Federal Food, Drug, and Cosmetic Act Requirements relating to Drugs for Human and Animal Use" (hereby incorporated by reference). Under this definition, a drug means (a) articles recognized in the official United States Pharmacopeia, official Homeopathic Pharmacopeia of the United States, or official National Formulary, or any supplement thereof; and (b) articles intended for use in the diagnosis, cure, mitigation, treatment, or prevention of disease in man or other animals; and (c) articles (other than food) intended to affect the structure of any function of the body of man or other animals; and (d) articles intended for uses as a component of any articles specified in clause (a), (b) or (c) above; but does not include devices or their components, parts or accessories.

In general, the PEGylated drug complexed with a carboxylated bioadhesive polymer in accordance with the present invention is generally stable at about pH 4 and below and readily falls apart at higher pH's when a significant fraction of the —COOH groups are ionized. That is, when subjected to an acidic environment, the complex formed between the PEGylated drug and the bioadhesive polymer is stable in that it does not readily dissociate; whereas when it is subjected to a non-acidic or neutral environment, the complex will dissociate at rates dependent on the degree of ionization of the —COOH groups. However, the pH at which the PEGylated drug/bioadhesive complex is stable may be controlled, for example, by appropriate selection of the bioadhesive polymer. For example, the use of polymethylacrylic acid (PMAAc) or polyethylacrylic acid (PEAAc), as opposed to polyacrylic acid (PAAc), will generally result in a complex that is stable at a pH approaching 7, thus further slowing the rate of drug release when the complex is exposed to body fluid or mucosal tissue having a pH of the same value.

Moreover, the addition of one or more of a free PEG (i.e., polyethylene glycol not covalently bonded to a drug), a polyvinylpyrrolidone, a polyacrylamide (including N-alkyl derivatives thereof such as —N($R_1$)($R_2$) derivatives where $R_1$ and $R_2$ are independently selected from hydrogen and $C_{1-8}$ alkyl) or polyvinyl alcohol (PVA) to the PEGylated drug/bioadhesive polymer complex, may further retard the rate at which PEGylated drug dissociates from the complex. Stated somewhat differently, the addition of one or more of a free PEG, polyvinylpyrrolidone, polyacrylamide (including its derivatives) or PVA may reduce the rate at which PEGylated drug becomes dissociated from the bioadhesive polymer, especially when the PEGylated drug includes PEGs below 10 kD in MW. Without prescribing to any particularly theory, it is believed that the addition of free PEG or other suitable polymer further condenses the PEGylated drug/bioadhesive polymer complex, thereby inhibiting the release of PEGylated drug when formed in an acidic environment and subsequently subjected to a non-acidic or neutral environment.

Accordingly, the PEGylated drug/bioadhesive polymer complexes of the present invention are particularly useful for the sustained and/or controlled release of a drug as that term has been defined above. In this embodiment, the PEGylated drug/bioadhesive polymer complex may be equilibrated in an acidic solution containing one or more agents, and then dried (e.g., in air, or lyophilized) to yield compositions in the form of particles and/or films. In the case of particles, such particles may generally have a diameter of less than 1 mm, and are more typically from about 0.1 mm to 0.5 mm in diameter. In some cases nanoparticles may form with a diameter of 50 nm or below. Depending upon its intended use, the larger particles may be further reduced in size by mechanical milling and grinding techniques.

The PEGylated drug/bioadhesive polymer complex and compositions formulated therefrom may be administered to the body of an animal (including man) in any suitable manner, such as by topical administration. Topical administration generally includes application to a mucosal tissue (such as the respiratory and alimentary tracts, rectum and vagina, eyes, nose, mouth and throat, lungs, gastro-intestinal tract, as well as open wounds) which contain sufficient water/ion content to hydrate the bioadhesive polymer. Moreover, the PEGylated drug/bioadhesive polymer complex and compositions thereof may be formulated using known formulation techniques in any manner suitable for its intended application. For example, the PEGylated drug-bioadhesive polymer complex may be suspended or emulsified within a solution containing an acceptable carrier or diluent, or combined with, for example, a solution, cream, gel, ointment or powder. Typically, suitable PEGylated drug/bioadhesive polymer complex concentrations in the formulations of these compositions range from 0.1% to 50% by weight, and preferably from 0.5% to 30% by weight.

The PEGylated drug/bioadhesive polymer complex and compositions thereof may also be formulated as a tablet, capsule, suppository, or even an aqueous (low pH) suspension. To this end, suppository formulations may be particularly suited for rectal administration of the PEGylated drug/bioadhesive polymer complex, while tablet and capsule form may be suitable for oral administration. Similarly, suspensions may be suitable for application to mucosal surfaces and/or tissues, such as eye, nose, vagina, lungs, mouth and throat, etc. The PEGylated drug/bioadhesive polymer complex may also be formulated for nasal, pulmonary or buccal administration by known techniques. Furthermore, the PEGylated drug/bioadhesive polymer complex may be formulated such that it may be implanted in the body of an animal by, for example, subcutaneous or intramuscular implantation, or may be implanted into bone.

In addition to use as vehicles for the sustained and controlled release of drugs, the PEGylated drug/bioadhesive polymer complex compositions of the present invention may have utility for a variety of other applications, including (but not limited to) uses relating to separation techniques, diagnostics, and bioreactions with immobilized ligands or reactant.

The following examples are provided for purposes of illustration, not imitation.

EXAMPLES

Materials and Methods:
  Papain MW 23,000, pI 8.75
    (available from Sigma)
  PEG Succinimidyl Succinate PEG (SS-PEG), MW 5,000
    Succinimidyl propionic acid PEG (SPA-PEG), MW 20,000
    Succinimidyl Succinate branched PEG (PG2-NHS), MW 2×20,000
    (available from Shearwater Polymers)
  Ionexchange chromatography:
  BioCad$^R$ PerSeptive Biosystems, Inc.
  Column Strong Cation Exchange
    POROS HS/M 4.6 mmD/100L, 1.66 ml
  Elution
  buffer:
    20 mM MES pH6.0, NaCl 0 to 1000 mM
  Mass spectrometry:
    Matrix Assisted Laser Deposition/Ionization-time of flight Mass
    Spectrometry. (MALDI-TOF-MS)

Papain, a model protein, was PEGylated by using NHS-activated PEG having molecular weights of 5 kD, 20 kD and branched 2×20 kD. Solutions of PEGylated papain, PAAc (450 kD), and/or free PEG (~18.5 kD) were mixed at pH 3.0 and cast and dried on the porous surface (pore size 8 μm) of the upper chamber of a Transwell$^R$ (Corning Costar). Release of PEGylated papain were examined in PBS, pH 7.4.

In the case of SS-PEG PEGylated to papain, for example, papain was dissolved in 10 ml of a borate buffer (100 mM, pH 8.5)(1.0 mg/ml, 4.35×10$^{-7}$ mol). A 10 times excess molar amount of SS-PEG (4.35×10$^{-6}$ mol, 21.8 mg) was added into the papain solution. After this mixture was allowed to rotate for 30 minutes at room temperature (i.e., 25–26° C.), unreacted papain and PEG were removed by cation exchange chromatography. A fraction of the PEGylated papain was collected with monitoring of absorbance at 280 nm. One or two PEG molecules were observed by the MALDI-TOF-MS.

Activity of PEGylated Papain:
   Substrate Nα-Benzoyl- L-Arginine-7-Amido-4-MethylCoumarin(BAAMCA) Sigma
   50 μl of Papain of PEGylated Papain, 100 μg/ml, was added into the 3 ml BAAMCA, of 50 μM, in 50 mM Tris-HCL, pH7.5 containing 5 mM L-Cysteine, and 2 mM EDTA and 1% DMSO. After the mixture was allowed to incubate for 0 to 60 min, at the room temperature, 25° C., fluorescent intensity at, λex 380 and λem 440, were measured.

Complexation:
   Transwell$^R$ Polycarbonate membrane, pore size 8.0 μm surface area 0.33 cm$^2$
   Corning Coster
   Elution buffer of PEGylated Papain was exchanged to citric buffer, pH3.0, 10 mM, by using the Sephadex-G column(PD-10$^R$). PAAc, MW 450 kD, or free PEG 18.5 kD was dissolved in distilled water and pH was adjusted to 3.0 by addition of NaOH. 2.0 mg of PAAc and 0.2 mg of PEGylated Papain and/or 0. 0.2, 0.4, 0.8 and 1.6 mg of free PEG were mixed in the upper chamber of Transwell$^R$, and dried at 37° C. for 24 hours.

Release:
   600 μl or 100 μl of PBS, pH 7.4 (10 mM PB, 2.7 mM KCl, 137 mM NaCl) was added into the lower or upper chamber of Transwell$^R$ respectively. The Transwell was allowed to shake at room temperature during the release experiments. After an appropriate interval, 400 μl of release medium from the lower chamber was sampled and the absorbance at 280 nm was measured.

In view of the foregoing materials and methods, the following more specific and illustrative examples are presented.

Example 1

RELEASE OF PEGYLATED PAPAIN FROM THE FORMULATIONS

This example corresponds to FIG. 1 which illustrates the percent release versus time of papain, 5 kD PEG-papain, 20 kD PEG-papain, and 2×20 kD PEG-papain, respectively, from their corresponding formulations (the formulations include polyacrylic acid (PAAc)), wherein:

Formulations: 0.2 mg Papain
   5 kD, 20 kD and 2×20 kDPEG-Papain
   2.0 mg 450 kD PAAc
   Mixed at pH 3.0 and cast.
   Release medium: PBS pH7.4 (Salt concentration 0.15M)

This example shows that the 5 kD PEGylated-papain is not slowed by the PAAc because the 5 kD PEG is too low in MW to complex with PAAc, while the 20 kD PEG-papain and the 2×20 kD PEG-papain are both retarded, because the 10 and 20 kD PEGs are large enough to form complexes with PAAc.

Example 2

RELEASE OF PAPAIN AND PEGYLATED PAPAIN—EFFECT OF A CONJUGATION OF PEG AND ADDITION OF FREE PEG

Figure 2:
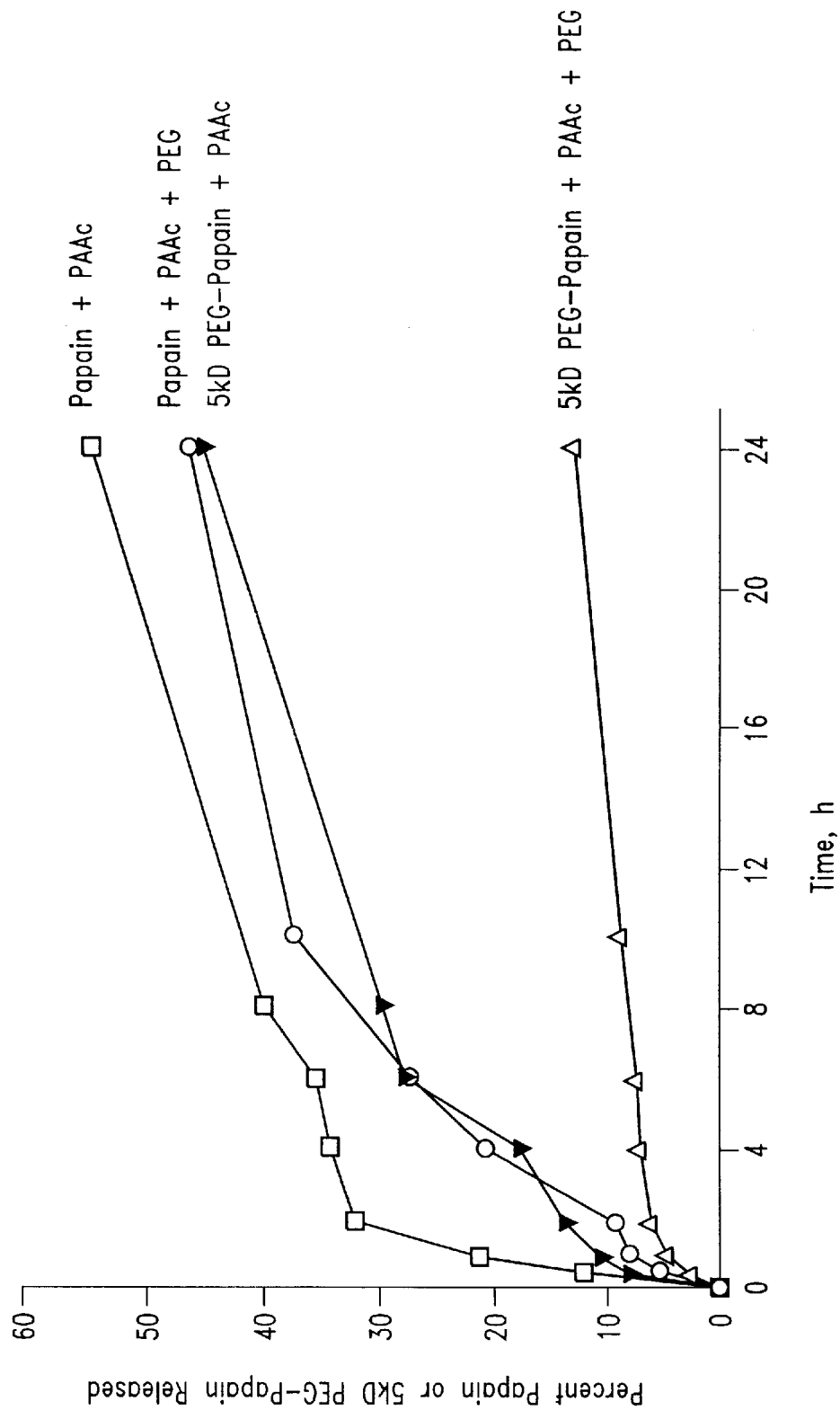
FIG. 2 illustrates the effect of the addition of 18.5 kD free PEG on the percent release versus time of papain and 5 kD PEG-papain, respectively, from their corresponding formulations (the formulations include polyacrylic acid (PAAc)).

This example corresponds to FIG. 2 which illustrates the effect of the addition of 18.5 kD free PEG on the percent release versus time of papain and 5 kD PEG-papain, respectively, from their corresponding formulations (the formulations include polyacrylic acid (PAAc)), wherein:

Formulations: 0.2 mg 5 kD PEG-Papain
   2.0 mg 450 kD PAAc
   0 and 0.8 mg 18.5 kD free PEG
   Mixed at pH 3.0 and cast
   Release medium: PBS pH7.4 (Salt concentration 0.15M)

This example shows that the addition of free 18.5 kD PEG to the 5 kD PEG-papain conjugate significanly retards its release rate, while it has only a slight retarding effect on the release of free papain.

Example 3

EFFECT OF FREE PEG ON TIE RELEASE OF PEGYLATED PAPAIN FROM THE FORMULATIONS

Figure 3:
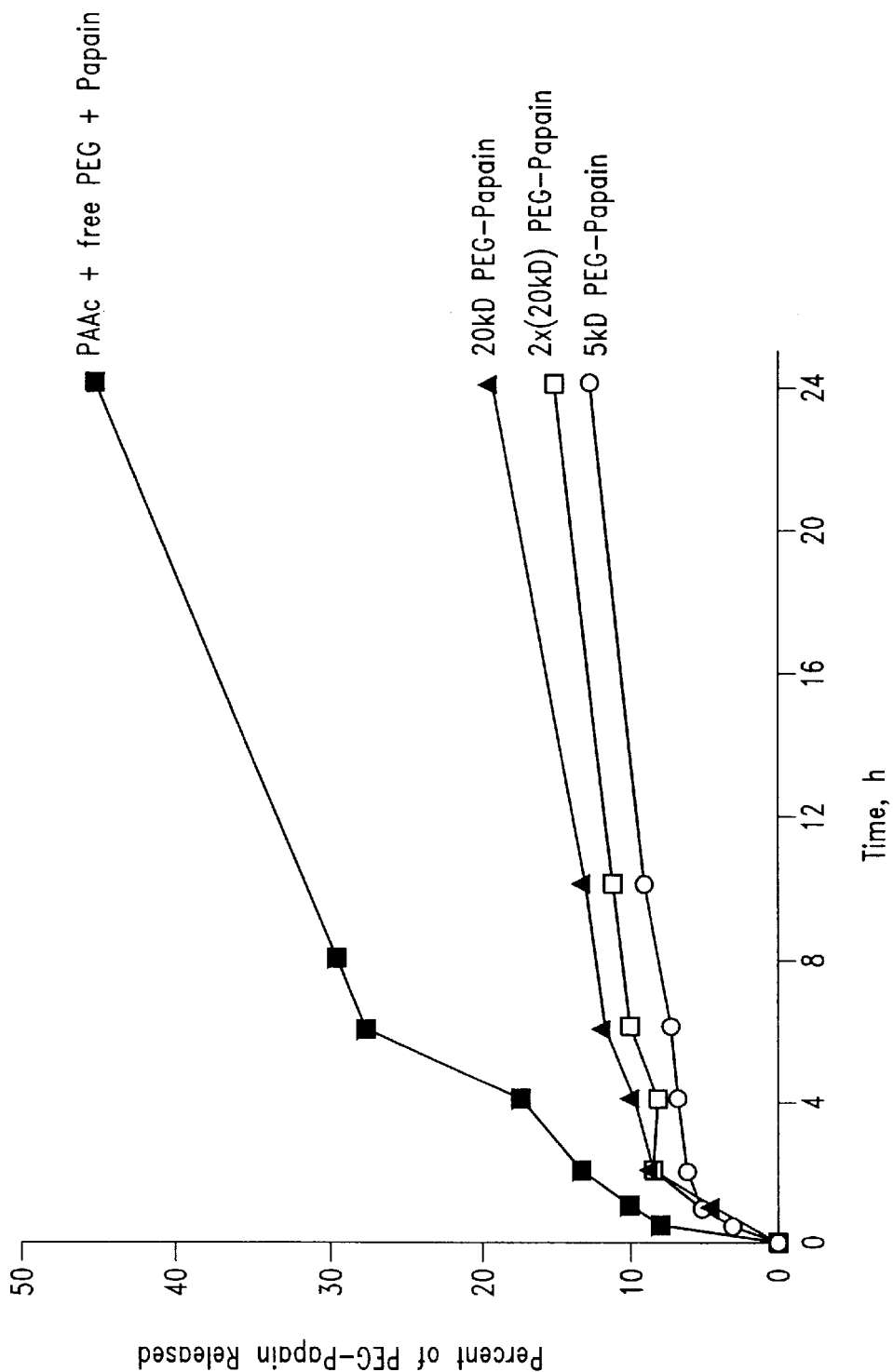
FIG. 3 illustrates the effect of the addition of 18.5 kD free PEG on the percent release versus time of papain, 5 kD PEG-papain, 20 kD PEG-papain, and 2×20 kDPEG-papain, respectively, from their corresponding formulations (the formulations include polyacrylic acid (PAAc)).

This example corresponds to FIG. 3 which illustrates the effect of the addition of 18.5 kD free PEG on the percent release versus time of papain, 5 kD PEG-papain, 20 kD PEG-papain, and 2×20 kD PEG-papain, respectively, from their corresponding formulations (the formulations include polyacrylic acid (PAAc)), wherein:

Formulations: 0.2 mg Papain
   5 kD, 20 kD and 2×20 kD PEG-Papain
   20. mg 450 kD PAAc
   0.8 mg 18.5 kD PEG
   Mixed at pH 3.0 and cast.
   Release medium: PBS pH7.4 (Salt concentration 0.15M)

This example shows that the addition of free 18.5 kD PEG does not significantly retard the release of 20 kD or 2×20 kD PEG-Papain, while the addition significantly retards the 5 kD PEG-Papain even below the 20 kD or 2×20 kD PEG-Papain.

Example 4

EFFECT OF FREE PEG ON THE RELEASE OF PEGYLATED PAPAIN FROM THE FORMULATIONS

Figure 4:
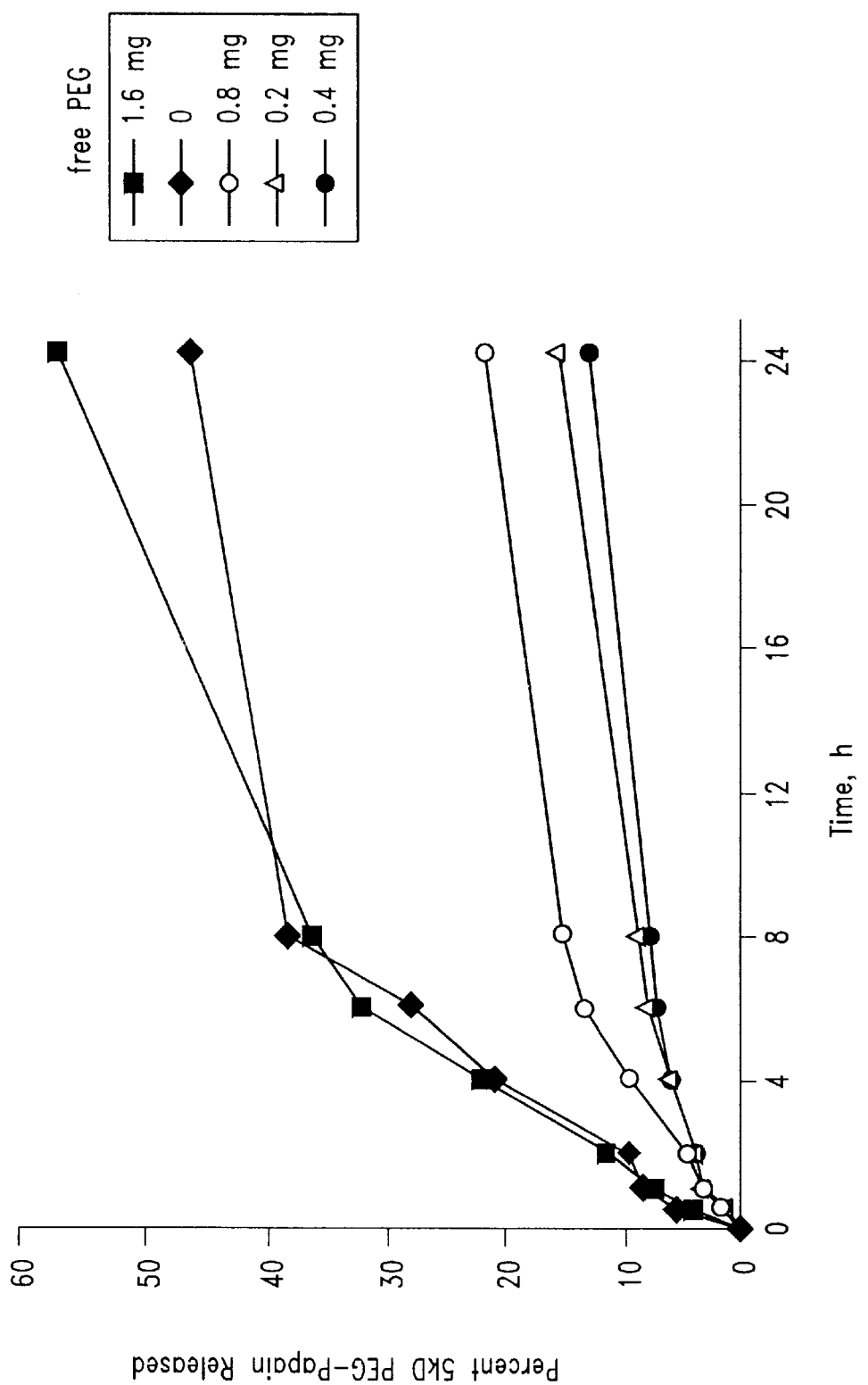
FIG. 4 illustrates the effect of the addition of different amounts of 18.5 kD free PEG on the percent release versus time of 5 kD PEG-papain from its corresponding formulations (the formulations includes polyacrylic acid (PAAc)).

This example corresponds to FIG. 4 which illustrates the effect of the addition of different amounts of 18.5 kD free PEG on the percent release versus time of 5 kD PEG-papain from its corresponding formulations (the formulations includes polyacrylic acid (PAAc)), wherein:

Formulations: 0.2 mg 5 kD PEG-Papain
   2.0 mg 450 kD PAAc
   0,0.2,0.4,0.8 and 1.6 mg 185 kD free PEG
   Mixed at pH 3.0 and cast.
   Release medium: PBS pH7.4 (Salt concentration 0.15M)

This example shows that there may be an optimum amount of free 18.5 kD PEG in any formulation, and in this particular formulation it is approximately 0.2–0.4 mg.

Example 5

EFFECT OF FREE PEG ON THE RELEASE OF PEGYLATED PAPAIN FROM THE FORMULATIONS

Figure 5:
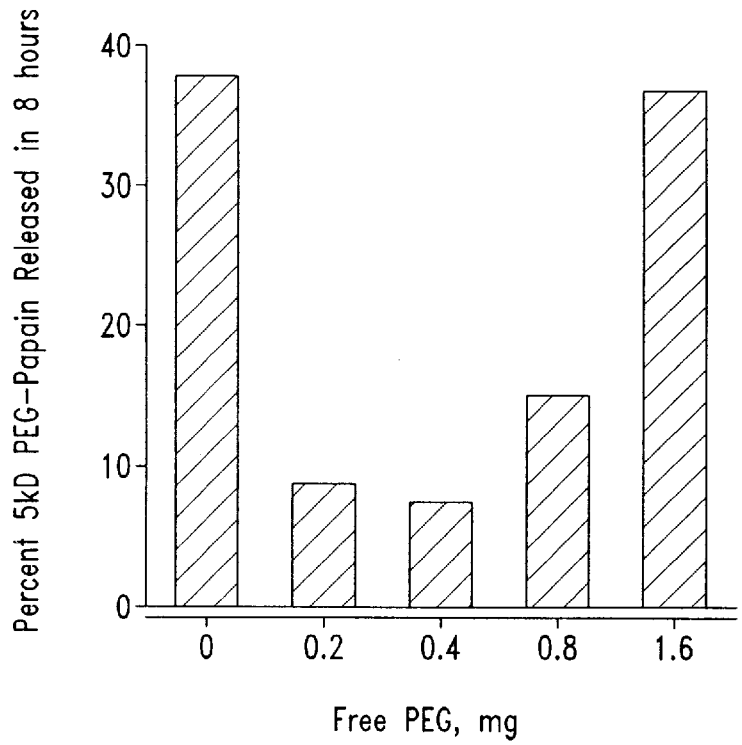
FIG. 5 provides a bar chart that illustrates the effect of the addition of different amounts of 18.5 kD free PEG on the percent released in an 8 hour period of 5 kD PEG-papain from its corresponding formulations as shown in FIG. 4.

This example corresponds to FIG. 5 which provides a bar chart that illustrates the effect of the addition of different amounts of 18.5 kD free PEG on the percent released in an 8 hour period of 5 kD PEG-papain from its corresponding formulations as shown in FIG. 4, wherein:

Formulations: 0.2 mg 5 kD PEG-Papain
2.0 mg 450 kD PAAc
0,0.2,0.4,0.8 and 1.6 mg 18.5 kD free PEG Mixed at pH 3.0 and cast.

Release medium: PBS pH7.4 (Salt concentration 0.15M)

This example plots the data of Example 4 in an alternative bar chart format.

Example 6

EFFECT OF FREE PEG ON THE RELEASE OF PEGYLATED PAPAIN FROM THE FORMULATIONS

Figure 6:
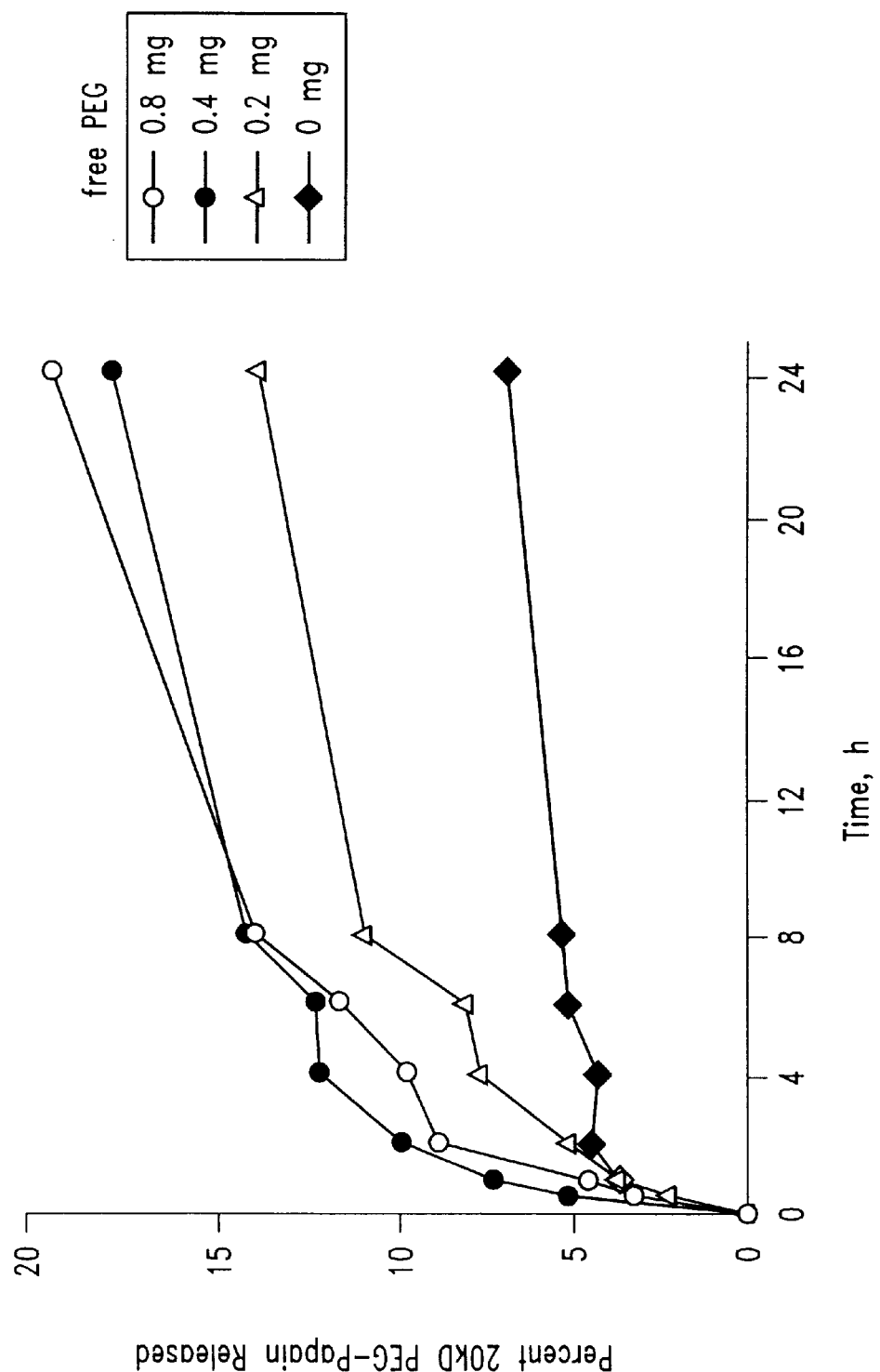
FIG. 6 illustrates the effect of the addition of different amounts of 18.5 kD free PEG on the percent release versus time of 20 kD PEG-papain from its corresponding formulations (the formulations includes polyacrylic acid (PAAc)).

This example corresponds to FIG. 6 which illustrates the effect of the addition of different amounts of 18.5 kD free PEG on the percent release versus time of 20 kD PEG-papain from its corresponding formulations (the formulations includes polyacrylic acid (PAAc)), wherein:

Formulations: 0.2 mg 20kD PEG-Papain
2.0 mg 45 kD PAAc
0,0.2,0.4,0.8 and 1.6 mg 18.5 kD free PEG Mixed at pH 3.0 and cast.

Release medium: PBS pH7.4 (Salt concentration 0.15M)

This example shows that the addition of free 18.5 kD PEG may only enhance the release rate of a 20 kD PEG-papain conjugate.

Example 7

EFFECT OF FREE PEG ON THE RELEASE OF PEGYLATED PAPAIN FROM THE FORMULATIONS

Figure 7:
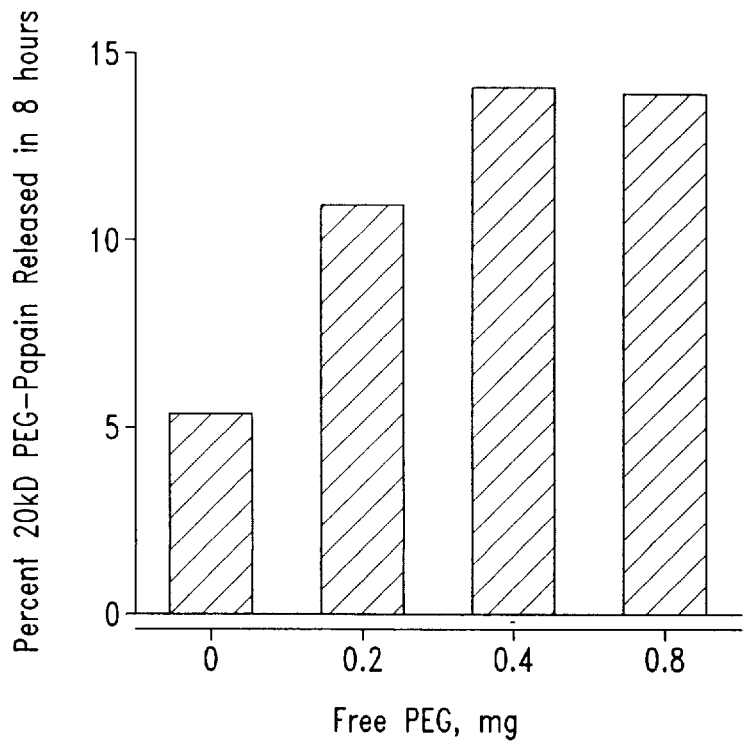
FIG. 7 provides a bar chart that illustrates the effect of the addition of different amounts of 18.5 kD free PEG on the percent released in an 8 hour period of 20 kD PEG-papain from its corresponding formulations as shown in FIG. 6.

This example corresponds to FIG. 7 which provides a bar chart that illustrates the effect of the addition of different amounts of 18.5 kD free PEG on the percent released in an 8 hour period of 20 kD PEG-papain from its corresponding formulations as shown in FIG. 6, wherein:

Formulations: 0.2 mg 20 kD PEG-Papain
2.0 mg 450 kD PAAc
0,0.2,0.4,0.8 and 1.6 mg 18.5 kD free PEG Mixed at pH 3.0 and cast.

Release medium: PBS pH7.4 (Salt concentration 0.15M)

This example plots the data of Example 6 in an alternative bar chart format.

Example 8

EFFECT OF FREE PEG ON THE RELEASE OF PEGYLATED PAPAIN FROM THE FORMULATIONS

Figure 8:
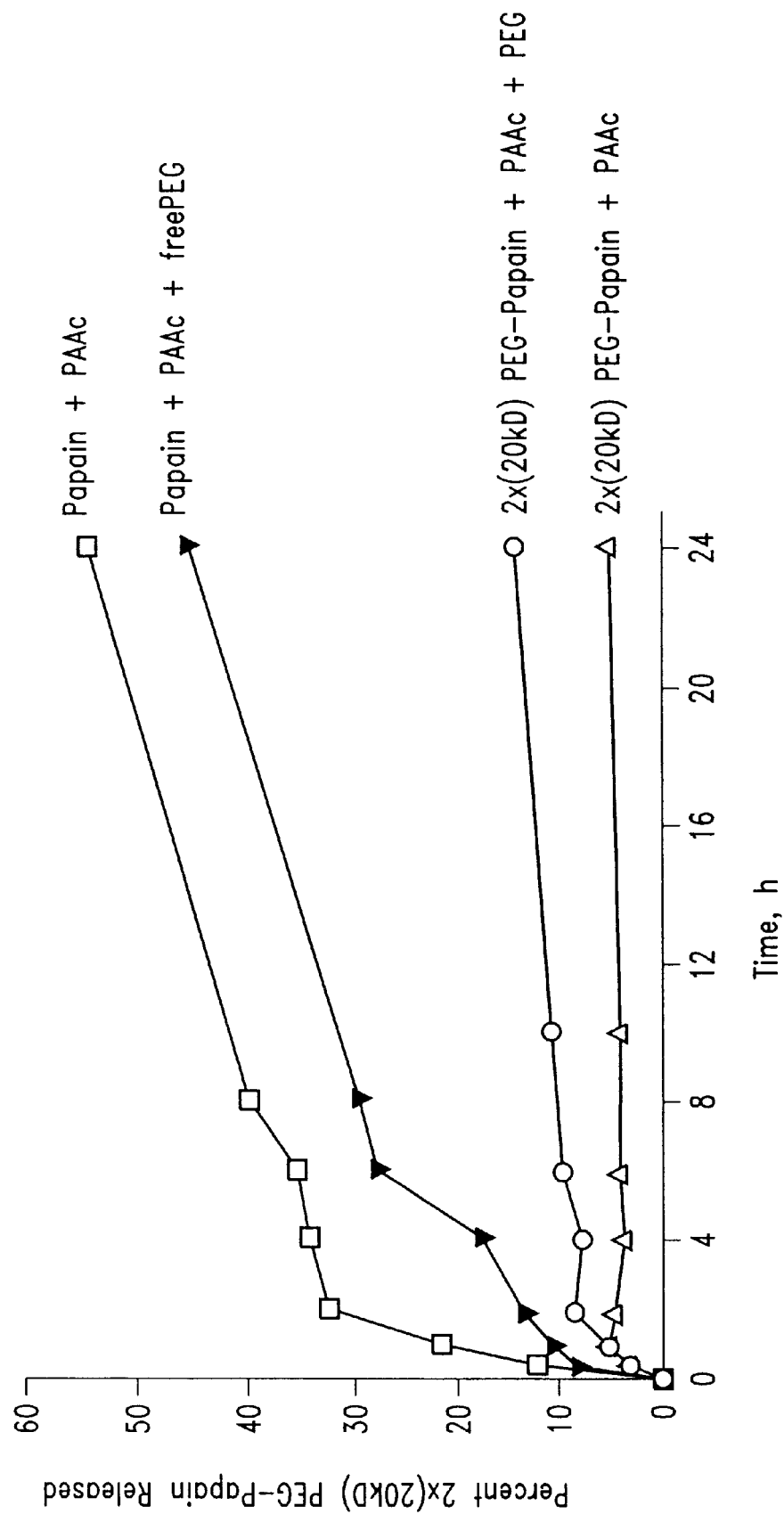
FIG. 8 illustrates the effect of the addition of 18.5 kD free PEG on the percent release versus time of papain and 2×20 kDPEG-papain, respectively, from their corresponding formulations (the formulations include polyacrylic acid (PAAc)).

This example corresponds to FIG. 8 which illustrates the effect of the addition of 18.5 kD free PEG on the percent release versus time of papain and 5 kD PEG-papain, respectively, from their corresponding formulations (the formulations include polyacrylic acid (PAAc)), wherein:

Formulations: 0.2 mg 2×20 kD PEG-Papain
2.0 mg 450 kD PAAc
0 and 0.8 mg 18.5 kD free PEG Mixed at pH 3.0 and cast.

Release medium: PBS pH7.4 (Salt concentration 0.15M)

This example shows that the addition of free 18.5 kD PEG does not lead to significantly retarded release of free papain, rather it speeds up the release of 2×20 kD PEG-papain.

Example 9

RELEASE OF PEGYLATED PAPAIN AND TRYPSIN INHIBITOR

Figure 9:
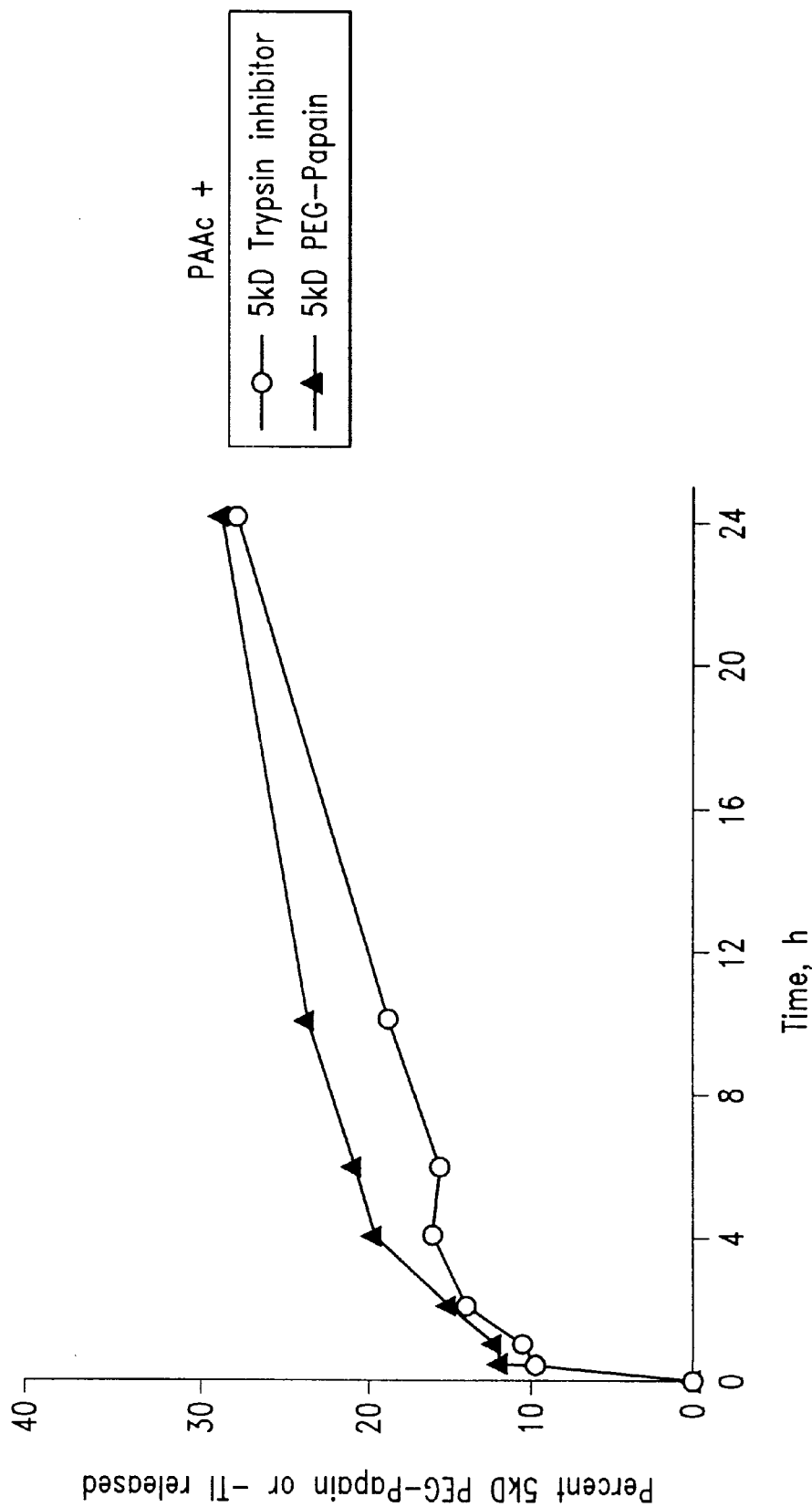
FIG. 9 illustrates the percent release versus time of 5 kD PEG-papain and 5 kD PEG-trypsin inhibitor, respectively, from their corresponding formulations (the formulations include polyacrylic acid (PAAc)).

This example corresponds to FIG. 9 which illustrates the percent release versus time of 5 kD PEG-papain and 5 kD PEG-trypsin inhibitor, respectively, from their corresponding formulations (the formulations include polyacrylic acid (PAAc)), wherein:

Formulations: 0.2 mg 5 kD PEG-Papain or -Trypsin inhibitor
2.0 mg 450 kD PAAc

Mixed at pH 3.0 and cast.

Release medium: PBS pH7.4 (Salt concentration 0.15M)

In this example, trypsin inhibitor is negatively charged at pH 7.4, whereas papain is positively charged. Thus, this example shows that in the absence of free 18.5 kD PEG, both the 5 kD PEG-trypsin inhibitor and 5 kD PEG-papain are released at about the same rate.

Example 10

EFFECT OF FREE PEG ON THE RELEASE OF PEGYLATED PAPAIN AND TRYPSIN INHIBITOR

Figure 10:
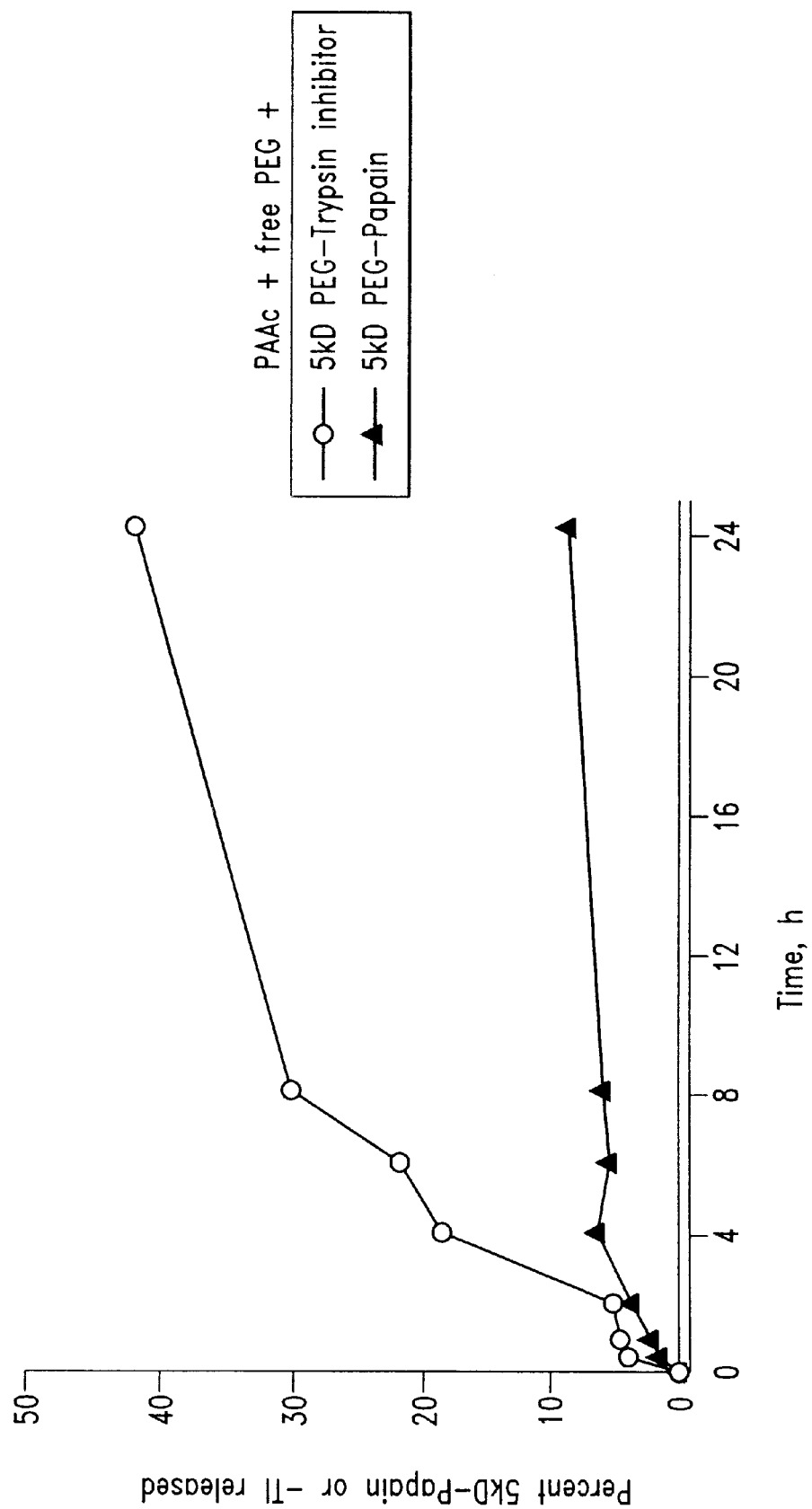
FIG. 10 illustrates the effect of the addition of 18.5 kD free PEG on the percent release versus time of 5 kD PEG-papain and 5 kD PEG-trypsin inhibitor, respectively, from their corresponding formulations (the formulations include polyacrylic acid (PAAc)).

This example corresponds to FIG. 10 illustrates the effect of the addition of 18.5 kD free PEG on the percent release versus time of 5 kD PEG-papain and 5 kD PEG-trypsin inhibitor, respectively, from their corresponding formulations (the formulations include polyacrylic acid (PAAc)), wherein:

Formulations: 0.2 mg 5 kD PEG-Papain or -Trypsin inhibitor
2.0 mg 450 kD PAAc
0.8 mg 18.5 kD free PEG Mixed at pH 3.0 and cast.

Release medium: PBS pH7.4 (Salt concentration 0.15M)

This example shows that when a condensing polymer such as free 18.5 kD PEG is added, the charge on the protein is also important to the retardation; that is, this example shows that the retardation of the 5 kD PEG-Papain (cationic at pH 7.4) is much greater than for 5 kD PEG-trypsin inhibitor (anionic at pH 7.4).

Example 11

RELEASE OF PEGYLATED PAPAIN AND TRYPSIN INHIBITOR FROM FORMULATIONS WITH PMAAC

Figure 11:
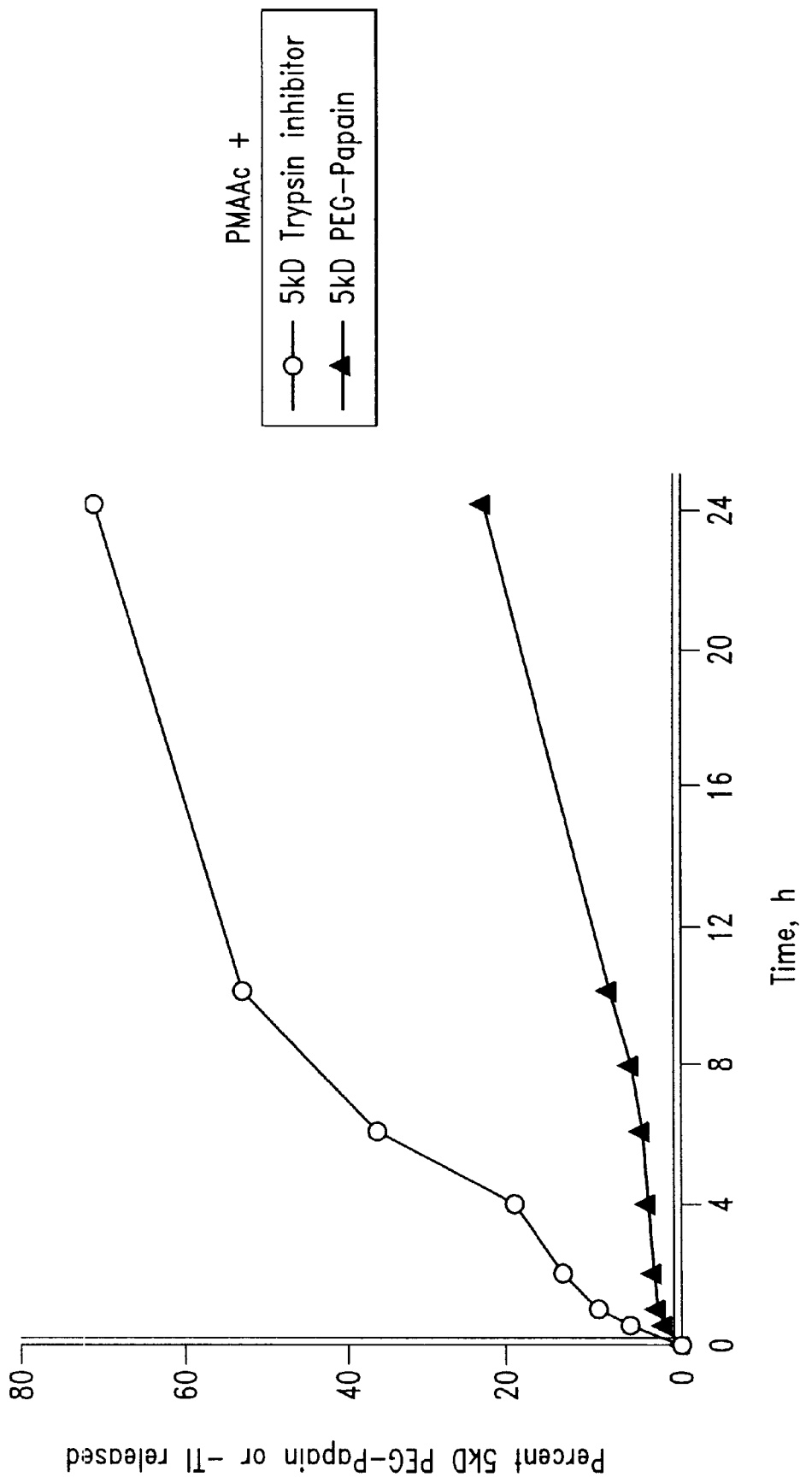
FIG. 11 illustrates the percent release versus time of 5 kD PEG-papain and 5 kD PEG-trypsin inhibitor, respectively, from their corresponding formulations (the formulations include polymethacrylic acid (PMAAc)).

This example corresponds to FIG. 11 which illustrates the percent release versus time of 5 kD PEG-papain and 5 kD PEG-trypsin inhibitor, respectively, from their corresponding formulations (the formulations include polymethacrylic acid (PMAAc)), wherein:

Formulations: 0.2 mg 5 kD PEG-Papain or -Trypsin inhibitor
2.0 mg 500 kD PMAAc

Mixed at pH 3.0 and cast.

Release medium: PBS pH7.4 (Salt concentration 0.15M)

This example shows that when PMAAc is substituted for PAAc, the postively-charged protein is released much more slowly than the negatively-charged protein in the absence of any added free PEG (Compare to FIGS. 9 and 10). This also shows that both ionic interactions between the protein and the bioadhesive polymer as well as the hydrophobic character of the bioadhesive polymer are important. The latter will also affect the pK of the —COOH group and the strength of the complex at pH 7.4.

Example 12

EFFECT OF PH ON THE RELEASE OF PEGYLATED PAPAIN FROM FORMULATIONS WITH PMAAc

Figure 12:
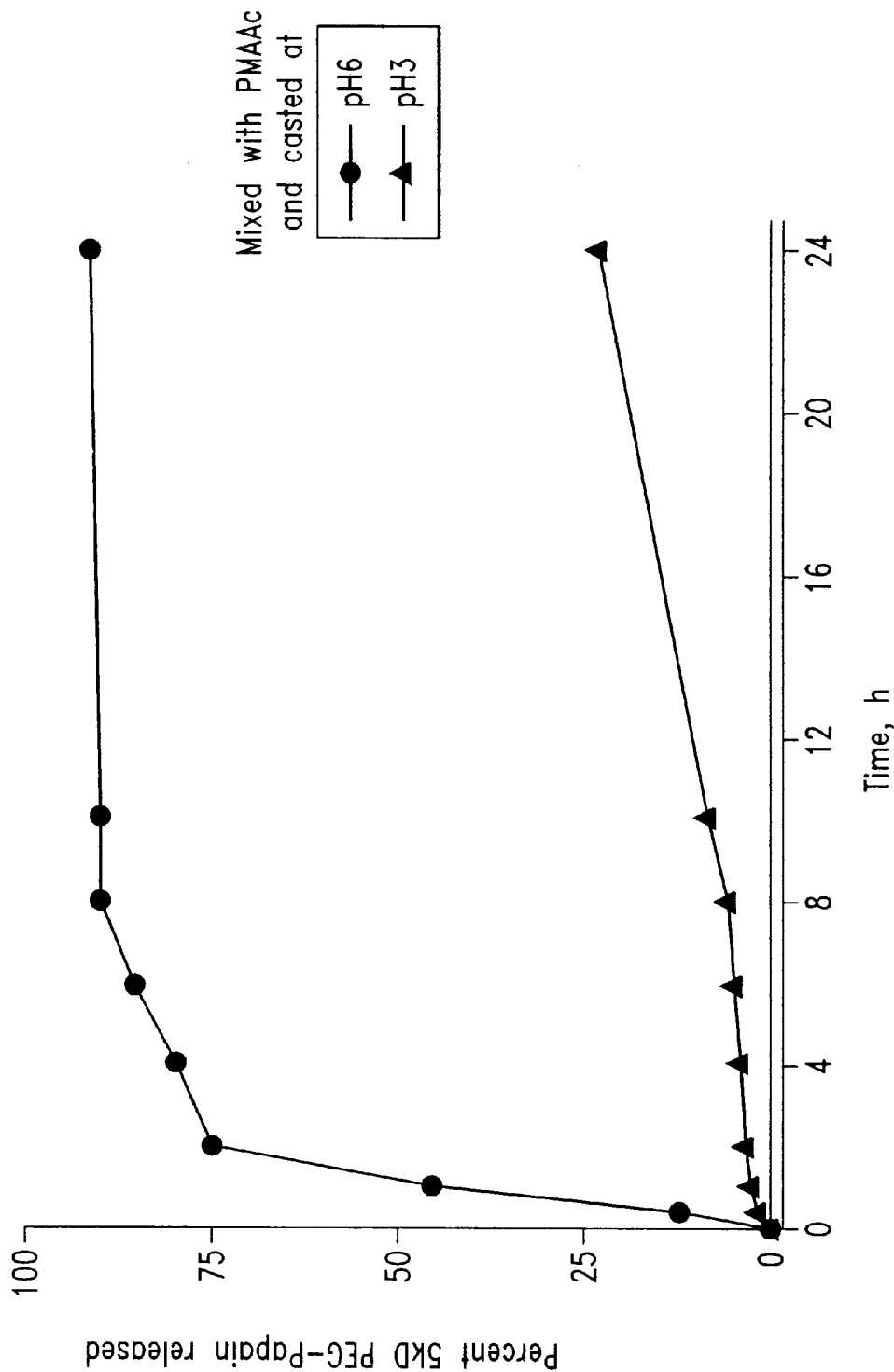
FIG. 12 illustrates the effect of casting the formulations at pH 3.0 and pH 6.0, respectively, on the release versus time of 5 kD PEG-papain from the respective formulations (the formulations include polymethacrylic acid (PMAAc)).

This example corresponds to FIG. 12 which illustrates the effect of casting the formulations at pH 3.0 and pH 6.0, respectively, on the release versus time of 5 kD PEG-papain; from the respective formulations (the formulations include polymethacrylic acid (PMAAc)), wherein:

Formulations: 0.2 mg 5 kD PEG-Papain
2.0 mg 5 kD PMAAc

Mixed at pH 3.0 or 6.0 and cast.

Release medium: PBS pH7.4 (Salt concentration 0.15M)

This example shows that the importance of casting the formulation at a low pH of 3.0 where the complex of PMAAc and PEG is strongly formed, as opposed to pH 6.0 where the complex may not be so strongly formed due to ionization of some of the —COOH groups.

Example 13

RELEASE OF PEGYLATED PAPAIN FROM THE PMAAc OR PMAAc GEL

Figure 13:
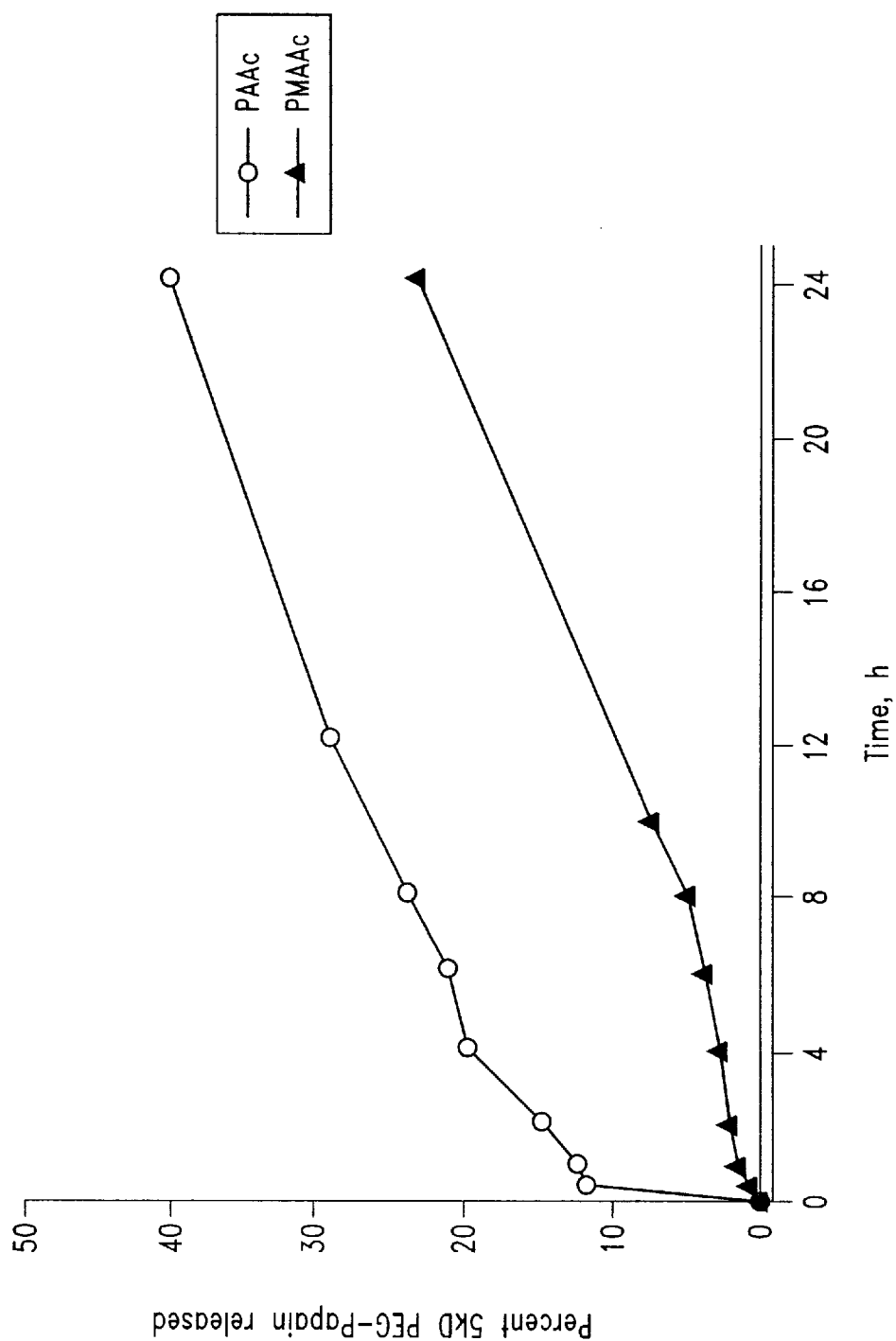
FIG. 13 illustrates the percent release versus time of 5 kD PEG-papain from formulations that include polyacrylic acid (PAAc) and polymethacrylic acid (PMAAc), respectively.

This example corresponds to FIG. 13 which illustrates the percent release versus time of 5 kD PEG-papain from formulations that include polyacrylic acid (PAAc) and polymethacrylic acid (PMAAc), respectively, wherein:

Formulations: 0.2 mg 5 kD PEG-Papain
2.0 mg 450 kD PAAc or 500 kD PMAAc

Mixed at pH 3.0 and cast.

Release medium: PBS pH7.4 (Salt concentration 0.15M)

This example shows (similar to FIGS. 9 and 11) that increased hydrophobic character of the bioadhesive polymer may lead to a stronger —COOH:PEG complex.

From the foregoing it will be appreciated that, although specific embodiments of the invention have been described herein for purposes of illustration, various modifications may be made without deviating from the spirit and scope of the invention. Accordingly, the invention is not limited except as by the appended claims.

What is claimed is:

1. A PEGylated drug complexed with a bioadhesive polymer, wherein the PEGylated drug comprises a polyethylene glycol covalently bonded to the drug, and wherein the bioadhesive polymer is selected from polyacrylic acid, polymethacrylic acid, polyethylacrylic acid and chitosan, or is a random block or graft copolymer comprising polyacrylic acid, polymethylacrylic or polycthylacrylic acid.

2. The PEGylated drug complexed with a bioadhesive polymer according to claim 1 wherein the polyethylene glycol has a molecular weight ranging from about 3 kD to about 50 kD.

3. The PEGylated drug complexed with a bioadhesive polymer according to claim 1 wherein the polyethylene glycol has a molecular weight ranging from about 5 kD to about 30 kD.

4. The PEGylated drug complexed with a bioadhesive polymer according to claim 1 wherein the polyethylene glycol has a molecular weight of about 5 kD.

5. The PEGylated drug complexed with a bioadhesive polymer according to claim 1 wherein the polyethylene glycol has a molecular weight of about 20 kD.

6. The PEGylated drug complexed with a bioadhesive polymer according to claim 1 wherein the polyethylene glycol has a molecular weight of about 40 kD.

7. The PEGylated drug complexed with a bioadhesive polymer according to claim 1 wherein the drug is a protein or a peptide.

8. The PEGylated drug complexed with a bioadhesive polymer according to claim 7 wherein the drug is a protein.

9. The PEGylated drug complexed with a bioadhesive polymer according to claim 1 wherein the drug is a hydrophobic drug.

10. The PEGylated drug complexed with a bioadhesive polymer according to claim 1 wherein the bioadhesive polymer is polyacrylic acid, polymethylacrylic or polyethylacrylic acid.

11. The PEGylated drug complexed with a bioadhesive polymer according to claim 1 wherein the bioadhesive polymer is polyacrylic acid.

12. The PEGylated drug complexed with a bioadhesive polymer according to claim 1 wherein the bioadhesive polymer is polymethylacrylic acid.

13. The PEGylated drug complexed with a bioadhesive polymer according to claim 1 wherein the bioadhesive polymer is polyethylacrylic acid.

14. The PEGylated drug complexed with a bioadhesive polymer according to claim 1 wherein the bioadhesive polymer is a random block or graft copolymer of one or more of polyacrylic acid, polymethylacrylic or polyethylacrylic acid.

15. The PEGylated drug complexed with a bioadhesive polymer according to claim 1 wherein the bioadhesive polymer is chitosan.

16. The PEGylated drug complexed with a bioadhesive polymer according to claim 1 wherein the PEGylated drug complexed with the bioadhesive polymer is stable at or below pH 4.

17. The PEGylated drug complexed with a bioadhesive polymer according to claim 1 wherein the PEGylated drug complexed with the bioadhesive polymer is stable up to about pH 7.

18. The PEGylated drug complexed with a bioadhesive polymer according to claim 1 wherein the PEGylated drug complexed with the bioadhesive polymer dissociates at or above about pH 7.

19. The PEGylated drug complexed with a bioadhesive polymer according to claim 1 in combination with free PEG, polyvinylpyrrolidone, polyacrylamide or N-alkyl derivatives thereof, or polyvinyl alcohol.

20. The PEGylated drug complexed with a bioadhesive polymer according to claim 19 wherein the free PEG has a molecular weight ranging from about 10 kD to about 500 kD.

21. The PEGylated drug complexed with a bioadhesive polymer according to claim 19 wherein the free PEG has a molecular weight ranging from about 10 kD to about 200 kD.

22. The PEGylated drug complexed with a bioadhesive polymer according to claim 19 wherein the free PEG has a molecular weight of about 18.5 kD.

23. The PEGylated drug complexed with a bioadhesive polymer according to claim 19 wherein the free polyvinylpyrrolidone has a molecular weight ranging from about 10 kD to about 500 kD.

24. The PEGylated drug complexed with a bioadhesive polymer according to claim 19 wherein the free polyvinylpyrrolidone has a molecular weight ranging from about 10 kD to about 200 kD.

25. The PEGylated drug complexed with a bioadhesive polymer according to claim 19 wherein the free polyvinylpyrrolidone has a molecular weight of about 18.5 kD.

26. The PEGylated drug complexed with a bioadhesive polymer according to claim 19 wherein the polyacrylamide or N-alkyl derivatives thereof has a molecular weight ranging from about 10 kD to about 500 kD.

27. The PEGylated drug complexed with a bioadhesive polymer according to claim 19 wherein the polyacrylamide or N-alkyl derivatives thereof has a molecular weight ranging from about 10 kD to about 200 kD.

28. The PEGylated drug complexed with a bioadhesive polymer according to claim 19 wherein the polyacrylamide or N-alkyl derivatives thereof has a molecular weight of about 18.5 kD.

29. The PEGylated drug complexed with a bioadhesive polymer according to claim 19 wherein the free polyvinyl alcohol has a molecular weight ranging from about 10 kD to about 500 kD.

30. The PEGylated drug complexed with a bioadhesive polymer according to claim 19 wherein the free polyvinyl alcohol has a molecular weight ranging from about 10 kD to about 200 kD.

31. The PEGylated drug complexed with a bioadhesive polymer according to claim 19 wherein the free polyvinyl alcohol has a molecular weight of about 18.5 kD.

32. A method of delivering a drug to a body fluid or mucosal tissue comprising contacting the body fluid or mucosal tissue with the PEGylated drug complexed with a bioadhesive polymer according to claim 1.

33. The method of delivering a drug according to claim 32 wherein the body fluid or mucosal tissue is fluid or tissue of the alimentary tract.

34. The method of delivering a drug according to claim 32 wherein the body fluid or mucosal tissue is fluid or tissue of the respiratory tract.

35. The method of delivering a drug according to claim 32 wherein the body fluid or mucosal tissue is fluid or tissue of the eye, nose, vagina, lung, mouth, or throat.

36. The method of delivering a drug according to claim 32 wherein the body fluid or mucosal tissue is fluid or tissue of an open wound.

\* \* \* \* \*

UNITED STATES PATENT AND TRADEMARK OFFICE
CERTIFICATE OF CORRECTION

PATENT NO. : 6,165,509
DATED : December 26, 2000
INVENTOR(S) : Allan S. Hoffman and Yoshiki Hayashi It is certified that error appears in the above-identified patent and that said Letters Patent is hereby corrected as shown below:

Claim 1, column 11,
Line 56 "polymethylacrylic or polycthylacrylic acid." should read -- polymethlylacrylic or polyethylacrylic acid. --

Signed and Sealed this

Twenty-fifth Day of September, 2001

Attest:

NICHOLAS P. GODICI
*Attesting Officer*    *Acting Director of the United States Patent and Trademark Office*